(12) United States Patent
Stepanek et al.

(10) Patent No.: US 11,806,165 B2
(45) Date of Patent: Nov. 7, 2023

(54) ELECTROPHYSIOLOGICAL AND STIMULATION ELECTRODE

(71) Applicant: Mayo Foundation for Medical Education and Research, Rochester, MN (US)

(72) Inventors: Jan Stepanek, Scottsdale, AZ (US); Michael J. Cevette, Cave Creek, AZ (US); Gaurav N. Pradhan, Fountain Hills, AZ (US); Samantha J. Kleindienst, Mesa, AZ (US); Kenneth H. Brookler, Norwalk, CT (US); Jamie M. Bogle, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 788 days.

(21) Appl. No.: 16/465,431

(22) PCT Filed: Nov. 30, 2017

(86) PCT No.: PCT/US2017/063855
§ 371 (c)(1),
(2) Date: May 30, 2019

(87) PCT Pub. No.: WO2018/102499
PCT Pub. Date: Jun. 7, 2018

(65) Prior Publication Data
US 2020/0000405 A1    Jan. 2, 2020

Related U.S. Application Data

(60) Provisional application No. 62/428,784, filed on Dec. 1, 2016.

(51) Int. Cl.
*A61B 5/24* (2021.01)
*A61B 5/00* (2006.01)
*A61N 1/04* (2006.01)

(52) U.S. Cl.
CPC ........ *A61B 5/6801* (2013.01); *A61B 2560/04* (2013.01); *A61B 2562/14* (2013.01); *A61B 2562/168* (2013.01); *A61N 1/0472* (2013.01)

(58) Field of Classification Search
CPC ..... A61B 5/291; A61B 5/6803; A61B 5/6814; A61B 5/316; A61B 5/369;
(Continued)

(56) References Cited

U.S. PATENT DOCUMENTS 4,362,165 A    12/1982   Carmon et al.
4,526,176 A *  7/1985   Bremer .................... A61B 5/25
                                                600/397

(Continued)

FOREIGN PATENT DOCUMENTS

WO    2012/140629 A1    10/2012

OTHER PUBLICATIONS

International Preliminary Report on Patentability received for PCT Patent Application No. PCT/US2017/063855, dated Jun. 13, 2019, 8 pages.

(Continued)

*Primary Examiner* — Joseph A Stoklosa
*Assistant Examiner* — Brian M Antiskay

(57) ABSTRACT

An electrode includes a body and a breakable container of contact-enhancing fluid on or in the body. The container is impermeable to the fluid, and is breakable in response to physical manipulation of the electrode to disperse the fluid into the body.

14 Claims, 1 Drawing Sheet

(58) Field of Classification Search
CPC . A61B 2562/0215; A61B 5/0006; A61B 5/25; A61B 2562/164; A61B 5/24; A61B 5/7203; A61B 5/282; A61B 2562/046; A61B 5/4839; A61B 5/6831; A61B 5/6843; A61B 5/259; A61B 5/6868; A61B 2562/227; A61B 5/053
USPC .................. 600/372, 382–393, 544–545
See application file for complete search history.

(56) References Cited

U.S. PATENT DOCUMENTS

| | | | |
|---|---|---|---|
| 4,928,690 A * | 5/1990 | Heilman | A61B 5/6831 600/509 |
| 6,201,982 B1 | 3/2001 | Menkes et al. | |
| 6,301,493 B1 * | 10/2001 | Marro | A61B 5/291 600/383 |
| 6,366,795 B1 * | 4/2002 | Bremer | A61B 5/25 600/397 |
| 8,428,682 B1 | 4/2013 | Rood et al. | |
| 9,192,313 B1 | 11/2015 | Lisy | |
| 9,326,695 B1 | 5/2016 | Kryzpow | |
| 2010/0016703 A1 * | 1/2010 | Batkin | A61N 1/0456 600/392 |
| 2013/0023749 A1 * | 1/2013 | Afanasewicz | A61B 5/6885 604/173 |
| 2017/0281036 A1 * | 10/2017 | Parvizi | A61B 5/721 |

OTHER PUBLICATIONS

International Search Report and Written Opinion received for PCT Patent Application No. PCT/US2017/063855, dated Mar. 14, 2018, 9 pages.

* cited by examiner

ELECTROPHYSIOLOGICAL AND STIMULATION ELECTRODE

CROSS-REFERENCE TO RELATED APPLICATION

This application is a national phase application of PCT Application No. PCT/US2017/063855, internationally filed on Nov. 30, 2017, entitled, ELECTROPHYSIOLOGICAL AND STIMULATION ELECTRODE, which claims the benefit of Provisional Application No. 62/428,784, filed Dec. 1, 2016, entitled, ELECTROPHYSIOLOGICAL AND STIMULATION ELECTRODE, both of which are incorporated herein by reference in their entireties.

FIELD OF THE INVENTION

The invention relates to electrodes for monitoring physiological signals in and/or for applying stimulation signals to the body of a human or other animal.

BACKGROUND

Electrodes used to receive or monitor electrical signals (i.e., physiological electrodes) and to apply electrical signals (i.e., stimulation electrodes) are generally known and disclosed, for example, in U.S. Pat. Nos. 8,428,682, 9,192,313 and 9,326,695, all of which are incorporated herein by reference in their entireties and for all purposes. Electrodes of these types typically have a body with a surface that engages the source or target of the electrical signals (e.g., on the skin of a patient). An electrical contact and lead wire can be used to couple the monitored signals from or the stimulation signals to the electrode body. The electrodes are attached to the electrical signal source or target, for example, by adhesive tape, an adhesive layer on the surface of the body that engages the electrical signal source or target, or other approaches such as a belt or band. So-called wet electrodes include a fluid such as liquid or gel having electrolytes or other substances in the body to enhance the electrical conductivity of the connection between the electrode body and the source or target of the electrical signals.

There remains a continuing need for improved electrodes. Electrodes that are easy to use, efficient to manufacture, and that provide effective electrical connections would be especially desirable.

SUMMARY

Embodiments of an electrode in accordance with the invention comprise a body and a container of contact-enhancing fluid on or in the body. The container is configured to disperse the contact-enhancing fluid into the body in response to physical manipulation.

DESCRIPTION OF THE INVENTION

Figure 1:
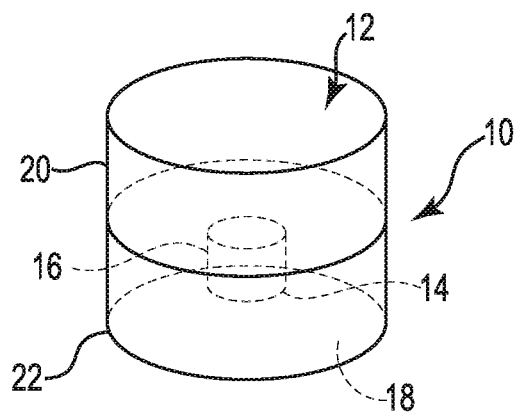
FIGS. 1-3 are illustrations of electrodes in accordance with embodiments of the invention.

FIG. 1 is an illustration of an electrode 10 in accordance with embodiments of the invention. As shown, electrode 10 includes a body 12 and a material structure or container 14 of contact-enhancing fluid 16. Although shown on the inside or interior of the body 12 in the illustrated embodiment, container 14 can be on the outside or other locations of the body in other embodiments. Body 12 can be formed from a porous or other wettable and fluid-retaining material. In embodiments, the body 12 is resilient. For example, body 12 can be formed from sponge-like polymer materials. A surface such as 18 of the body 12 is configured to be positioned on the surface of a human or other animal (e.g., skin or other tissue of a patient) at the target location where physiological signals are to be monitored and/or stimulation signals are to be applied.

The fluid 16 in the container 14 enhances the nature of the electrical contact between the body 12 (e.g., at surface 18) and the surface on which the electrode 10 is placed. For example, in embodiments the fluid 16, which can be a liquid and/or a gel, can include an electrolyte that minimizes or reduces the impedance of the electrical connection. The fluid 16 can include materials such as but not limited to liquids such as water or saline and/or hydrogel that alleviate irritation or other undesired effects on the skin or other tissue on which the electrode is placed. The container 14 is configured to retain the fluid 16 prior to use of the electrode 10, and to release the fluid in response to physical manipulation when is it desired to use the electrode. Following the release of the fluid 16, the fluid can disperse throughout the body 12, including to the surface 18, allowing the electrode 10 to function as a wet electrode. In embodiments, for example, the container 14 is a blister pack container formed of material (e.g., polymer) that is impermeable to the fluid 16, and that can be broken when the electrode 10 is squeezed and/or rubbed in the hand of the user. In other embodiments the container 14 is material such as but not limited to hydrogel or liquid (e.g., water) that retains the fluid 16 until the fluid is forced out of the material when the electrode 10 is squeezed with the hand of the user.

The illustrated embodiment of the body 12 is formed from two members 20 and 22 that are joined together (e.g., by adhesive). One or both of the members 20 and 22 can include a recess for the container 14, thereby enclosing the container within the body. Other embodiments of electrode 10 include other configurations for positioning the container 14 within the body 12. Yet other embodiments of electrode 10 include adhesive sections (e.g., with peel-off release liners) or other structures that can be used to facilitate attachment of the electrode.

Figure 2:
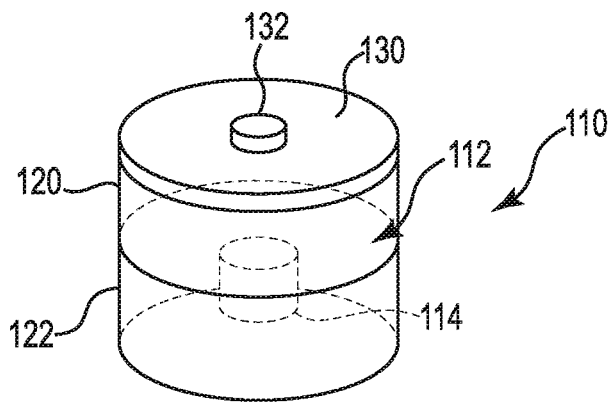

FIG. 2 is an illustration of an electrode 110 in accordance with embodiments of the invention. Electrode 110 includes a contact 130 on the body 112. Contact 130 includes a post 132 and can be used to electrically connect the electrode 110 to a monitoring or stimulation device through a lead wire (not shown). Other embodiments of electrode 110 (not shown) have pre-wired lead wires. Yet other embodiments can be used in wireless systems. Other than the contact 130, electrode 110 can be the same as or similar to electrode 10 described above, and similar features are shown with similar reference numbers.

Figure 3:
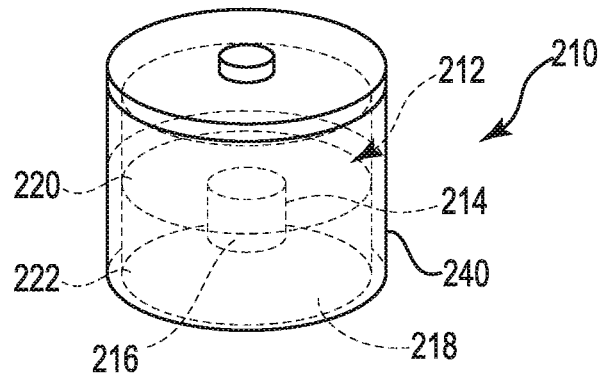

FIG. 3 is an illustration of an electrode 210 in accordance with embodiments of the invention. Electrode 210 includes a resilient shell 240 around at least portions of the body 212 (e.g., around the side portions, while exposing the surface 218). The shell 240 is formed from material that is generally impervious to the fluid 216, thereby enhancing the convenience of use of the electrode by enabling a user to handle the electrode while minimizing contact with the fluid. Other than the shell 240, electrode 210 can be the same as or similar to electrodes 10 and 110 described above, and similar features are shown with similar reference numbers. For example, electrode 210 includes a container 214 and members 220 and 222.

Electrodes in accordance with embodiments of the invention offer a number of advantages. For example, in addition to providing effective electrical contacts, they are convenient and easy to use. They can also be efficiently manufactured. The electrodes and components thereof can be reusable or disposable in embodiments.

Although the invention has been described with reference to preferred embodiments, those of skill in the art will recognize that changes can be made in form and detail without departing from the spirit and scope of the invention.

The invention claimed is:

1. An electrode, comprising: a body formed of a three-dimensional mass of porous and resilient material, the three-dimensional mass of porous and resilient material defining a first surface portion configured to be positioned on a surface of a subject and a second surface portion, wherein the three-dimensional mass of porous and resilient material extends between the first surface portion and the second surface portion, wherein the body is configured to be physically manipulated by a user squeezing and/or rubbing the porous and resilient material in a hand of the user; and
   an electrical contact on the second surface portion of the body;
   a container of contact-enhancing fluid on or in the body and in contact with the body; and
   wherein the body and the container are configured to cause the contact-enhancing fluid to disperse into the three-dimensional mass of porous and resilient material of body, including to the first surface portion, when the body is physically manipulated in the hand of the user.

2. The electrode of claim 1, wherein the container is impermeable to the contact-enhancing fluid and breakable in response to the physical manipulation.

3. The electrode of claim 1, wherein the container is in the body.

4. The electrode of claim 3, wherein the three-dimensional mass of porous and resilient material includes first and second members, and a recess in one or both of the first and second members for receiving the container.

5. The electrode of claim 1, and further including a resilient shell around at least portions of the three-dimensional mass of porous and resilient material, wherein the shell is generally impervious to the contact-enhancing fluid.

6. The electrode of claim 1, wherein the contact-enhancing fluid includes conductive fluid such as an electrolyte.

7. The electrode of claim 1, wherein the contact-enhancing fluid includes one or more of a liquid or a gel.

8. The electrode of claim 1, wherein the container is hydrogel.

9. The electrode of claim 1, wherein the body substantially consists of the mass of three-dimensional porous and resilient material.

10. A method for preparing an electrode having a body formed of a three-dimensional mass of porous and resilient material, the three-dimensional mass of porous and resilient material defining a first surface portion configured to be positioned on a surface of a subject and a second surface portion, wherein the three-dimensional mass of porous and resilient material extends between the first surface portion and the second surface portion, and contact-enhancing fluid, comprising physically manipulating the electrode by hand, including squeezing and/or rubbing the three-dimensional mass of porous and resilient material in a hand of the user, to disperse the contact-enhancing fluid throughout the three-dimensional mass of porous and resilient material.

11. The method of claim 10, wherein the electrode comprises a container of the contact-enhancing fluid, and the method further comprises breaking the container while physically manipulating the electrode.

12. The method of claim 10, wherein the body substantially consists of the mass of three-dimensional porous and resilient material.

13. An electrode, comprising:
   a body formed of a three-dimensional mass of porous and resilient material, the three-dimensional mass of porus and resilient material defining a first surface portion configured to be positioned on a surface of a subject and a second surface portion, wherein the three-dimensional mass of porous and resilient material extends between the first surface portion and the second surface portion, wherein the body is configured to be physically manipulated by a user squeezing and/or rubbing the porous and resilient material in a hand of the user; and
   an electrical contact on the second surface portion of the body; and
   contact-enhancing fluid on or in the body, wherein the fluid is configured to be dispersed throughout the three-dimensional mass of porous and resilient material in response to the physical manipulation of the electrode.

14. The electrode of claim 13, wherein the body substantially consists of the mass of three-dimensional porous and resilient material.

* * * * *